United States Patent [19]

Braus et al.

[11] 4,119,789

[45] Oct. 10, 1978

[54] FLAME RETARDANT COMPOSITIONS

[75] Inventors: Harry Braus, Cincinnati, Ohio; Jay R. Woltermann, Memphis, Tenn.

[73] Assignee: National Distillers and Chemical Corporation, New York, N.Y.

[21] Appl. No.: 698,619

[22] Filed: Jun. 21, 1976

Related U.S. Application Data

[62] Division of Ser. No. 505,287, Sep. 12, 1974, Pat. No. 3,979,545.

[51] Int. Cl.² .................. C07C 125/06; C07C 127/15; C07C 103/24; C07C 103/47
[52] U.S. Cl. ............................. 560/161; 260/45.85 A; 260/45.9 NC; 260/553 R; 260/558 R; 260/561 R
[58] Field of Search .............. 260/45.85 A, 45.59 NC, 260/553 R, 482 C, 558 R, 561 R; 424/300, 320, 322; 560/161

[56] References Cited

U.S. PATENT DOCUMENTS

| | | | |
|---|---|---|---|
| 2,706,733 | 4/1955 | Reid | 260/553 R |
| 2,724,643 | 11/1955 | Morris et al. | 260/558 R |
| 3,147,219 | 9/1964 | Paterson | 260/561 R |
| 3,160,653 | 12/1964 | Benning et al. | 260/558 R |
| 3,221,044 | 11/1965 | Hoch | 260/558 R |
| 3,288,822 | 11/1966 | Hall et al. | 260/561 R |
| 3,333,970 | 8/1967 | Green | 260/40 |
| 3,752,845 | 8/1973 | Beermann et al. | 260/482 C |
| 3,850,878 | 11/1974 | Murtha et al. | 260/45.85 A |
| 3,865,761 | 2/1975 | Schnabel | 260/45.85 A |
| 3,931,311 | 1/1976 | Thomas | 260/553 R |
| 3,962,246 | 6/1976 | Borer et al. | 260/482 C |
| 3,966,965 | 6/1976 | Sellstedt et al. | 260/561 R |
| 3,969,230 | 7/1976 | Scharf | 260/482 C |

OTHER PUBLICATIONS

J. Medicinal Chem., vol. 9, pp. 892–911, Nov. 1966.

*Primary Examiner*—V. P. Hoke
*Attorney, Agent, or Firm*—Kenneth D. Tremain

[57] ABSTRACT

The flame resistance of synthetic fibers and solid polymers are improved by treatment with a halogen containing amide having the formula

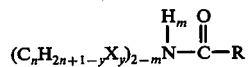

wherein R is lower alkoxy; lower alkoxy carbonyl;

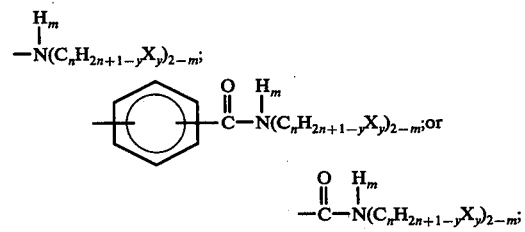

X is chlorine or bromine; $m$ is 0 or 1; $n$ is 1–6; and $y$ is 1–13.

7 Claims, No Drawings

FLAME RETARDANT COMPOSITIONS

This is a divisional of application Ser. No. 505,287, filed Sept. 12, 1974, now U.S. Pat. No. 3,979,545.

BACKGROUND OF THE INVENTION

There is a great demand for fire retardant fibers. Cotton and rayon fibers, fabrics and garments probably compose the most flammable textile materials in use today. Many of the synthetic fibers as well as fibers of animal origin are less flammable but the problem of imparting fire retardancy thereto still exists.

It is generally accepted that the earliest attempts to reduce the flammability of cellulose textiles was made by Wilde in 1753 in England and later by Gay-Lussac in France in 1821. Their studies revealed the utility of various inorganic salts as fire retardant agents for cellulose. The development of semi-durable and durable fire retardant finishes began in the early 1900s but it was not until the 1950s that truly durable finishes, i.e., resistant to ordinary laundering, were available. The very early finishes were based on the precipitation of metal oxides within the fiber. Later developments included the discovery that combinations of certain halogenated compounds and antimony oxide formed an efficient and moderately durable fire retardant for cellulose.

We have now discovered a group of halogenated compounds which can impart an effective degree of flame retardance to synthetic fibers and solid polymers. In U.S. Pat. No. 3,644,493, there is described 2,3-dihaloalkyl compounds as flame retardant for various natural and synthetic fibers. All of these compounds are esters of allyl alcohol, which are then halogenated in contrast to the present compounds which are derivatives of allyl and diallyl amines and are, in fact, halogenated amides.

Accordingly, it is the object of this invention to provide a new group of compounds for the imparting of flame resistance to synthetic fibers. This and other objects of the invention will become apparent from the following detailed description of the invention.

SUMMARY OF THE INVENTION

This invention pertains to the imparting of flame resistance to synthetic fibers and more particularly pertains to improving the flame resistance of synthetic fibers by treatment with a halogen containing amide compound.

DESCRIPTION OF THE PREFERRED EMBODIMENTS

The compounds employed in the present invention are halogen containing amides of the formula

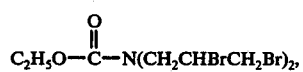

In the foregoing formula, R can be lower alkoxy, i.e., of 1–6 carbon atoms; lower alkoxy carbonyl;

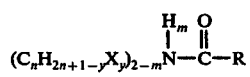

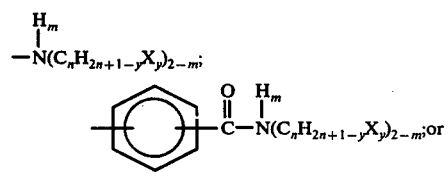

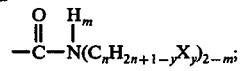

X can be chlorine or bromine; $m$ can be 0 or 1; $n$ can be 1–6; and $y$ can be 1–13.

Illustrative of lower alkoxy groups which can be R in the foregoing formula are methoxy, ethoxy, propoxy, etc. Bis($\beta,\gamma$-dibromopropyl) ethyl carbamate,

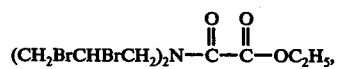

is exemplary of such compounds.

In those compounds where R is lower alkoxy carbonyl, i.e.,

the lower alkyl moiety (A) contains 1–6 carbon atoms. Methoxy carbonyl, ethoxy carbonyl, propoxy carbonyl, etc. are illustrative of such radicals and N,N-bis($\beta,\gamma$-dibromopropyl) ethyl oxamate,

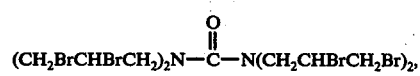

is exemplary of the resulting compounds.

In the compounds in which R is represented by the group

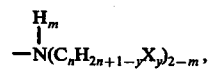

the number of carbon atoms is, as before, 1–6 and the halogen can be chlorine or bromine. N,N-bis($\beta,\gamma$-dibromopropyl)amino is illustrative of such a radical and tetra($\beta,\gamma$-dibromopropyl)urea,

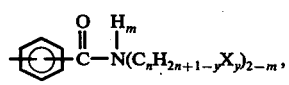

is illustrative of the resulting compound. Where R is represented by the the group

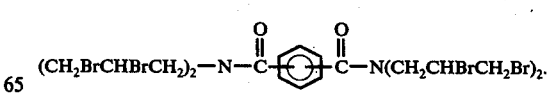

the lower alkyl and halogen groups are as described above and the arylene is phenylene. Illustrative of such a compound is N,N,N',N'-tetrakis($\beta,\gamma$-dibromopropyl)isophthalamide, $$(CH_2BrCHBrCH_2)_2-N-\overset{O}{\overset{\|}{C}}-\underset{}{\bigcirc}-\overset{O}{\overset{\|}{C}}-N(CH_2CHBrCH_2Br)_2.$$

In the compounds in which R is represented by the group

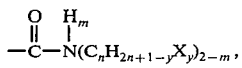

the lower alkyl and halogen are as described above. N-(dibromopropyl) amido is illustrative of such a radical and N,N'-bis(β,γ-dibromopropyl) oxamide,

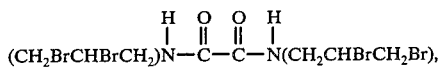

is exemplary of the resulting compound.

The compounds employed in the present invention are known and can be prepared by conventional means.

The foregoing halogen containing amides are employed in solution form or in the form of an aqueous emulsion. In either case, the amides can vary in concentration over a wide range of from about 5–25 weight percent and preferably about 10–20 weight percent.

Suitable solvents for the halogen containing amides include the halogenated hydrocarbons such as trichloroethylene, perchloroethylene, methylene chloride, and the like; ketones such as acetone, methyl ethyl ketone, and the like; ether, and any other organic solvents in which the halogen containing amides are soluble.

Suitable emulsifying agents for maintaining the amides in aqueous emulsions include anionic, cationic and non-ionic dispersing agents or surfactants. Suitable non-ionic surfactants include the alkyl phenoxy poly(ethyleneoxy)ethanols, and the dialkyl phenoxy poly(ethyleneoxy)ethanols, preferably those wherein the alkyl substituents have 5–12 carbon atoms and which have 1–20 ethyleneoxy groups. Typical members are octyl phenoxy poly(ethyleneoxy)ethanol, nonyl phenoxy poly(ethyleneoxy)ethanol and dodecyl phenoxy poly(ethyleneoxy)ethanol. Also useful are the fatty acid esters of polyhydric alcohols or ether alcohols such as glycerol monostearate; esters of ethylene glycol, diethylene glycol, triethylene glycol and polyethylene glycol such as the condensation product of oleic acid with ethylene oxide; and fatty esters of sugar alcohols. Suitable anionic surfactants include the alkali metal alkyl benzene sulfonates such as sodium and potassium dodecyl benzene sulfonate; the alkali metal alkyl sulfates such as sodium lauryl sulfate; the sulfonated aliphatic polyesters, free acids of complex phosphate esters, sodium salts of complex phosphate esters and sodium salts of disproportionated wood resin. Suitable cationic surfactants include the fatty amides of monoethanol amines, fatty nitriles and fatty acid amides such as olein morpholide. Also useful as cationic agents are the polyoxy ethylated alkyl amines.

The synthetic fibers which can be treated in accordance with the present invention include the polyamides such as 6-, and 6,6-nylons, polyesters, polyolefins such as polypropylene or polyethylene, acrylics, triacetates such as arnel, and blends of natural and synthetic fibers such as cotton/polyester and wool/polyester. Mixed fabrics and fibers may be similarly treated.

The fibers may be in any of the usual forms and in natural bulk, interwoven, knitted or felted form as for example in the form of a staple fiber or continuous filament in bulk form, or in the form of tow, rope, yarns, slubblings, warps, fabrics and felts and the like, and treated as a wound package, running length, fiber stock, bulk, etc.

The fire retardant compounds of the instant invention can be applied to the synthetic textile fibers by a variety of procedures and using different kinds of equipment. While the individual steps and equipment can vary with the different procedures, in each case, the fiber is immersed in the solution or emulsion and the compound is deposited therefrom as, for example, by removing the solvent by evaporation or vaporization. In one suitable procedure, a multitude of synthetic textile yarn ends from a creel are passed through a container in which is found the solution of the halogen containing amide. Thereafter the yarn ends are passed between squeeze rolls to remove excess solution and then passed over a multitude of drying cans which are usually maintained at a temperature of about 150°–230° F. Similarly, the fibers can be treated by dipping them into the solution or emulsion, followed by drying.

The temperature at which the fibers are immersed in the solution or emulsion can vary over a wide range of from about 30°–100° C.; preferably the temperature is about 90°–100° C. and most preferably ambient temperature is employed. The immersion time can similarly vary over a wide range of from about ½–2 hours, preferably about one-half hour. The fibers are maintained immersed in the solution or emulsion until an effective flame resistant amount of the halogen containing amide, generally about 5–20 weight percent, and preferably about 10–15 weight percent of the dried impregnated fibers, has been picked up by the fibers. The halogen containing compounds of this invention can also be used to impart flame resistance to solid thermoplastic polymers such as polyethylene, polypropylene, polyesters and copolymers and blends thereof, nylons, polyurethanes, etc. If desired, about 5–20% of an antimony compound such as $Sb_2O_3$ is used in conjunction with the halogen containing compound to achieve a higher degree of flame resistance in these solid thermoplastic polymers.

The flame resistant solid thermoplastic polymer compositions may be prepared by utilizing conventional methods such as internal mixers such as Banbury, continuous mixers, mixing extruders, and two-roll mills.

The following Examples are set forth in order to further illustrate the present invention. Throughout this specification and claims, all temperatures are in degrees centigrade and all parts and percentages are by weight unless otherwise specified.

EXAMPLE 1

Bis(β,γ-dibromopropyl)ethylcarbamate was prepared by the bromination of N,N-(diallyl)ethylcarbamate as follows.

Charged into a one liter, 3-necked flask equipped with the necessary adjuncts were diallylamine, 48.6 g (0.5 mole), triethylamine, 50.6 g (0.5 mole) and 200 ml of ether. This was cooled to 0° C. and ethylchloroformate, 54.3 g (0.5 mole) was added slowly dropwise with constant stirring. The addition took 3½ hours, maintaining a temperature of 0° C. An additional 350 ml of ether was added to maintain fluidity. After warming to room temperature, the solid amine salt was filtered and the ether distilled from the filtrate. The resulting product was purified by distillation under reduced pressure. B.P. 40.5°–41° C. at 0.1 mm Hg. - Yield 71%.

Charged into a one liter, 3-necked flask equipped with a stirrer, $N_2$ inlet, thermometer, dropping funnel and condenser were N,N-diallylethylcarbamate, 57.8 g (0.342 mole), and 300 ml of chloroform. This was cooled to 0° C. and with vigorous stirring, bromine, 109.3 g (0.684 mole) was added dropwise. When the addition was complete, the bath was warmed to room temperature and allowed to stand overnight. The chloroform was then distilled and finished at 0.5 mm pressure. Yield 81.2%.

A sample was submitted for mass spectra which showed a compound of mass 485 containing 4 bromines. This confirms the structure of the compound.

Bis($\beta,\gamma$-dibromopropyl)ethylcarbamate (40 g ) is dispersed in ethylene glycol (80 g) using as emulsifier, Duponal OS (2 g) an amine long chain alcohol sulfate. The mixture is heated with stirring until a homogeneous dispersion is obtained. The solution is then cooled to room temperature. Before use, this dispersion is emulsified with water (150 g) preferably using a colloid mill.

EXAMPLE 2

N,N-bis($\beta,\gamma$-dibromopropyl)ethyloxyamate was prepared by the bromination of N,N-diallylethyl oxamate as follows.

Ethyloxalate, 146.1 g (1.0 mole), was charged into a 3-necked flask equipped with a mechanical stirrer, dropping funnel, condenser and drying tube. Diallylamine, 97.2 g (1.0 mole) was slowly added with constant stirring. There was a moderate exotherm during the addition until approximately one-half the amine was added, at which time the temperature declined. When the addition was complete, the bath was heated to 80°-90° C. for 4 hours and then cooled by standing overnight.

The product was then fractionated and vacuum distilled and the portion boiling at 105°-106° C. at 1 mm Hg was collected. The product was submitted for mass spectra determination which showed a mass of 197 and the expected fragments of the desired product, N,N-diallylethyloxamate.

The N,N-diallylethyloxamate, 77.3 g (0.39 mole), dissolved in 100 ml of chloroform, was charged to a one liter, 3-necked flask equipped with a stirrer, thermometer, dropping funnel, condenser and drying tube. The solution was cooled to 4° C. and bromine, 124.7 g (0.78 mole), was slowly added. When all the bromine was added, the chloroform was distilled at atmospheric pressure. The remaining chloroform was removed under reduced pressure (water pump). The residue was taken up in benzene, filtered and evaporated under a stream of $N_2$. M.P. 160° C. (with decomposition). Mass spectra analysis confirmed the desired compound.

N,N-bis($\beta,\gamma$-dibromopropyl)ethyloxamate (30 g) is dissolved in perchloroethylene (180 ml) using Triton X-100 (5 g) which is an octylphenoxypolyethoxy ethanol.

EXAMPLE 3

Tetra($\beta,\gamma$-dibromopropyl)urea was prepared by the bromination of bis(diallyl)urea as follows.

Charged under dry $N_2$ to a one liter, 3-necked flask equipped as in the previous preparation, were diallylamine, 44.3 g (0.456 mole) and triethylamine, 46.1 g (0.456 mole), in 100 ml of dry benzene. This was cooled with stirring to 0° C. and to this was carefully added phosgene in benzene, 237.8 g (0.228 mole). The pot temperature was maintained at 0°-5° C. by the regulation of addition rate. When the addition was complete, the amine hydrochloride was filtered off, the benzene washed with $H_2O$ and dried. The benzene was then removed under reduced pressure. Yield - 41.3 g 82%-83% theory. Mass spectra confirmed the expected structure.

Bromination of bis(diallyl)urea was effected as follows: charged into a dry one liter, 3-necked flask with the usual equipment were bis(diallyl)urea, 39.4 g (0.18 mole), and 100 ml chloroform. This was cooled to 0° C. with constant stirring. Then, 115.1 g (0.72 mole) bromine in 50 ml of chloroform was slowly added, maintaining a temperature of 0°-5° C. Additional amounts of chloroform (total 150 ml) were added to keep the reaction mixture fluid. When the addition was complete, the batch was stirred for one-half hour until it reached room temperature. The solvent was distilled. The residue consisted of a thick syrup which set up to an amorphous solid.

Tetra($\beta,\gamma$-dibromopropyl)urea (25 g) was dissolved in 100 ml of perchloroethylene using as emulsifying agent, Triton X-100.

EXAMPLE 4

N,N,N',N'-tetrakis($\beta,\gamma$-dibromopropyl)isophthalamide was prepared by the bromination of tetraallylisophthalamide. This latter compound was prepared as follows.

Charged, under dry $N_2$ to a one liter, 3-necked flask equipped with a stirrer, $N_2$ inlet, thermometer, dropping funnel and condenser, were diallylamine, 88.6 g (0.912 mole), and triethylamine, 92.3 g (0.912 mole), in 300 ml of ether. Isophthaloyl chloride, 92.5 g (0.456 mole), dissolved in 200 ml of ether, was slowly added maintaining a temperature of approximately 0°-5° C. Addition was complete in 3½ hours. Evaporation of the ether yielded 129.6 g of product - 87.5% of theory.

Bromination of the bis amide was accomplished as follows: charged under dry nitrogen to a one liter, 3-necked flask equipped with a stirrer, $N_2$ inlet, dropping funnel and condenser was tetraallylisophthalamide, 123.8 g (0.38 mole) and 200 ml of chloroform. This was cooled with stirring to 0° C. and there was slowly added bromine, 243.0 g (1.52 mole), diluted with chloroform. The temperature was kept at $-5°$ to 5° C. The product began to separate out and more solvent was added. When the addition was completed, the batch was stirred at room temperature for 1 hour. The mixture was then heated to remove solvent. There remained a thick syrup which set up to an amorphous fluid.

N,N,N',N'-tetrakis($\beta,\gamma$-dibromopropyl)isophthalamide (30 g) is emulsified in water using IGEPAL CA-420 (5 g) an octylphenoxypoly(ethyleneoxy)ethanol. Emulsification is hastened by use of heat and ultrasonic vibration.

EXAMPLE 5

N,N'-bis($\beta,\gamma$-dibromopropyl)oxamide was prepared by the bromination of N,N'-bis(allyl)oxamide. The latter compound was prepared as follows:

Charged to a 2-liter, 3-necked flask were allylamine, 114.2 g (2.0 mole) and 150 ml of ethanol. To this solution, ethyl oxalate, 146 g (1.0 mole) in 50 ml of ethanol was slowly added with stirring. The reaction was exothermic and when the temperature reached 40° C., cooling was applied to 20°-+° C. at which temperature the remaining ethanol was added. The mixture was cooled to room temperature and allowed to stand overnight. The batch was further cooled in ice and filtered and the filter cake washed with ethanol and air dried. Yield - 123.7 g, M.P. 156.5°-157.5° C.

The bromination was carried out in the usual manner using glacial acetic acid as the solvent. The yield was 102.1 g (83.5% of theory), M.P. 222°–224° C. Mass spectra confirmed the structure in both molecular weight and bromine content.

N,N'-bis(β,γ-dibromopropyl)oxamide (30 g) is dissolved in 110 ml of perchloroethylene using IGEPAL CA-420 (5 g).

EXAMPLE 6

The compound bis(β,γ-dibromopropyl)ethylcarbamate is most readily applied to a fabric material by exhaustion from an aqueous system. The solution is prepared as shown in Example 1. A cloth of polyester is placed in the bath which is then heated to 90°–100° C. A polyester softener such as sorbitol, sulfonated castor oil, low molecular weight polyethylene or silicone textile lubricants, may be added. The absorption of the carbamate by the fibers is low at low heat and high at higher temperatures. The fabric is kept submerged for 1–2 hours, after which the fabric is removed and dried in an air circulating oven at 100°–110° C. The cloth is weighed to determine the add on, usually 5% to 10% increase is sufficient to render the fabric flame retardant. The pick-up can be regulated to yield the desired degree of flame retardance.

EXAMPLE 7

A weighed nylon 6,6 cloth is submerged in the solution prepared in Example 2 and soaked for about 15–20 minutes. The cloth is then dried in an air circulating type oven and weighed for total pick-up. 7% was the amount of pick-up on weight of goods (O.W.G.). The cloth, when held vertically, would not support combustion when the source of flame was removed.

EXAMPLE 8

Example 7 was repeated except that the flame retardant compound is tetra(β,γ-dibromopropyl)urea and the fabric used is cellulose triacetate. The treated fabric is rendered flame retardant as measured by the vertical flame test.

EXAMPLE 9

The solution prepared in Example 4 using N,N,N',N'-tetrakis(β,γ-dibromopropyl)isophthalamide may be used directly. A polyester cloth is placed in the solution which is heated to boiling for 1 hour. The solution is cooled (or optionally, the cloth may be removed when hot) and dried at 100° C. in an air circulating oven. Over 6% O.W.G. pick-up imparts flame retardance as measured by vertical flame test.

EXAMPLE 10

A solution of N,N'-bis(β,γ-dibromopropyl)oxamide in perchloroethylene (prepared in Example 5) is used. A piece of nylon cloth is soaked in the solution for about 20 minutes. The cloth is oven dried using air circulation and weighed. The pick-up (O.W.G.) is about 8%. The cloth passes the vertical flame test and untreated cloth burns.

various changes and modifications can be made in the process and products of this invention without departing from the spirit and the scope thereof. The various embodiments set forth herein were for the purpose of further illustrating the invention but were not intended to limit it.

We claim:

1. A halogen containing amide of the formula

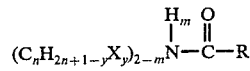

wherein
R is lower alkoxy,
lower alkoxy carbonyl,

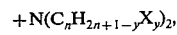

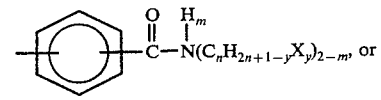

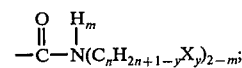

X is chlorine or bromine;
$m$ is 0 or 1;
$n$ is 1–6;
$y$ is 1–13; and
when R is lower alkoxy and $n$ is 1 and $m$ is 0, $y$ is 2–3.

2. The amide of claim 1 wherein the lower alkoxy radical contains 1–6 carbon atoms and the lower alkoxy carbonyl radical contains 2–7 carbon atoms.

3. The amide of claim 2 wherein said amide is N,N-bis(β,γ-dibromopropyl)ethyloxamate.

4. The amide of claim 2 wherein said amide is bis(β,γ-dibromopropyl) ethyl carbamate.

5. The amide of claim 2 wherein said amide is tetra(β,γ-dibromopropyl)urea.

6. The amide of claim 2 wherein said amide is N, N, N¹, N¹ - tetrakis (β, γ-dibromopropyl) isophthalamide.

7. The amide of claim 2 wherein said amide is N,N,'-bis(β, γ-dibromopropyl)oxamide.